US010538548B2

(12) United States Patent
Krammer et al.

(10) Patent No.: US 10,538,548 B2
(45) Date of Patent: Jan. 21, 2020

(54) MATERIAL MIXTURE CONTAINING RUBUSOSIDE OR ALPHA GLYCOSYLRUBUSOSIDE, FOR ENHANCING SWEET TASTE

(71) Applicant: SYMRISE AG, Holzminden (DE)

(72) Inventors: Gerhard Krammer, Holzminden (DE); Christoph Sabater, Holzminden (DE); Thomas Riess, Holzminden (DE); Jakob Ley, Holzminden (DE); Thorsten Geißler, Einbeck (DE)

(73) Assignee: SYMRISE AG, Holzminden (DE)

( * ) Notice: Subject to any disclaimer, the term of this patent is extended or adjusted under 35 U.S.C. 154(b) by 433 days.

(21) Appl. No.: 15/313,724

(22) PCT Filed: Jun. 11, 2015

(86) PCT No.: PCT/EP2015/063092
§ 371 (c)(1),
(2) Date: Nov. 23, 2016

(87) PCT Pub. No.: WO2015/189346
PCT Pub. Date: Dec. 17, 2015

(65) Prior Publication Data
US 2017/0190727 A1    Jul. 6, 2017

(30) Foreign Application Priority Data

Jun. 13, 2014  (EP) .................................... 14172306

(51) Int. Cl.
A23L 27/00       (2016.01)
A23L 27/30       (2016.01)
C07H 15/24       (2006.01)
C12P 19/56       (2006.01)

(52) U.S. Cl.
CPC ............. *C07H 15/24* (2013.01); *A23L 27/36* (2016.08); *A23L 27/84* (2016.08); *A23L 27/88* (2016.08); *C12P 19/56* (2013.01); *A23V 2002/00* (2013.01)

(58) Field of Classification Search
CPC .... C07H 15/24; C12Y 204/0109; C12P 19/56; C12P 19/18; A23L 27/36; A23L 27/88; A23L 27/84
See application file for complete search history.

(56) References Cited

U.S. PATENT DOCUMENTS

| 2008/0305052 A1* | 12/2008 | Ley ............................ A61K 8/02 424/49 |
| 2013/0078192 A1* | 3/2013 | Backes .................. A61K 8/498 424/49 |
| 2013/0084252 A1* | 4/2013 | Backes .................. A61K 47/22 424/49 |

FOREIGN PATENT DOCUMENTS

| EP | 2 353 403 A1 | 8/2011 |
| EP | 2 386 211 A1 | 11/2011 |
| JP | 2002-045145 A | 2/2002 |
| WO | 2012/112180 A1 | 5/2012 |
| WO | WO-2013133689 A1 * | 9/2013 ............... A23L 2/60 |

OTHER PUBLICATIONS

JP 2002-045145 English Translation. 2002.*
Hirono, S., Chou, W.-H., Kasai, R., Tanaka, O., Tada, T. 1990. Sweet and Bitter Diterpene-Glucosides from Leaves of Rubus suavissimus. Chem. Pharm. Bull. vol. 38, pp. 1743-1744.*
Darise et al, "Enzymic Transglucosylation of Rubusoside and the Structure-Sweetness Relationship of Steviol-Bisglycosides," Agric. Biol. Chem., 48(10), 2483-2488, 1984.
Ohtani et al, "Further Study on the 1,4-α-Transglucosylation of Rubusoside, a Sweet Steviol-Bisglucoside from Rubus suavissimus," Agric. Biol. Chem., 55(2), 449-453, 1991.
Chou et al, "Quantitative and Fingerprint Analyses of Chinese Sweet Tea Plant (*Rubus suavissimus* S. Lee)," J. Agric. Food Chem. 2009, 57, 1076-1083.

* cited by examiner

*Primary Examiner* — Nikki H. Dees
(74) *Attorney, Agent, or Firm* — Polsinelli PC

(57) ABSTRACT

The invention relates to novel substance mixtures which can be used as aroma compositions to enhance the sweet taste of oral preparations.

9 Claims, No Drawings

MATERIAL MIXTURE CONTAINING RUBUSOSIDE OR ALPHA GLYCOSYLRUBUSOSIDE, FOR ENHANCING SWEET TASTE

FIELD OF THE INVENTION

The invention is in the field of foodstuffs and relates to novel substance mixtures that are used as aroma compositions to enhance the sweet taste of orally consumable preparations.

STATE OF THE ART

*Rubus* glycosides are obtained from the leaves of the plant *Rubus suavissimus* S. Lee (Chinese blackberry) and are a complex mixture of different glycosides of the diterpene steviol. *Rubus* glycosides are used as calorie-free sweeteners whereas the pure rubusoside has a sweetening power which is 200 times that of sugar. The Chinese blackberry is native to South East Asia where its sweetening power has been known for a long time. Nowadays, the plant is cultivated on a large scale in the Chinese regions of Guang-xi and Guang-dong.

Products containing *Rubus* glycosides as sweeteners are sufficiently known from the state of the art. Attempts to increase the content of rubusoside by concentration processes are also known. For example, mixtures of rubusoside and steviosides and their use as sweeteners are described in the two patent applications EP 2641479 and WO 2012/177727.

The subject matter of WO 2013/133689 is a chromatographic process for the purification of steviol glycosides.

However, the quality of *Rubus* glycosides that are available on the market is characterised by the fact that all of them have a bitter, sometimes astringent aftertaste and an insufficient sweetening effect, which still makes it difficult to broadly use them. *Rubus* glycosides can be used to mask unpleasant taste impressions (EP 2,386,211), however, this is not working on its own. Preparations for improvement using simple *Rubus* extracts have been described (EP 2,641,479), but this has not lead to an improvement of the sweetening profile.

Formerly, individual products of an alpha-glycosylation of rubusoside were isolated and evaluated for their taste (Ohtani, K.; Aikawa, Y.; Ishikawa, H.; Kasai, R.; Kitahata, S.; Mizutani, K.; Doi, S.; Nakaura, M.; Tanaka, O., Further study on the 1,4-alpha-transglucosylation of rubusosides, a sweet steviol-bisglucoside from *Rubus suavissimus*. Agric. Biol. Chem. 1991, 55, (2), 449-453), however, the purification until a single substance is obtained is extremely complex and commercially not reasonable, thus not allowing any applicablity.

It is further referred to the following documents of the state of the art:

JP 2002 045145 A (TOYO SUGAR REFINING) discloses a process for providing a sweet mixture of *Stevia* extract, which substantially contains stevioside, rebaudioside A, rebaudioside C, and dulcoside A. During the performance of this process the rhamnose part of dulcoside A is hydrolysed, producing rubusoside ([0014]), which results in a sweet mixture with a minute quantity of rubusoside (Table 1). This mixture exhibits a reduced bitterness and an increased sweet taste ([0019]) and may, therefore, be used in an aroma composition ([0035]). In addition, rubusoside is reacted into corresponding glucosylated products by an enzymatic reaction ([0024]).

The publication Agricultural and Biological Chemistry, Vol. 48(10), p 2483-2488 (1984) discloses the products of a rubusoside-transglucosylation reaction, which do not only contain different rubusoside glucosides during the reaction, but also reacted rubusoside (paragraph 2, p. 2484). The production of the glucosylated products by CGTase system and the evaluation of their sweet taste are also described (part of the experiment on page 2486 and of Table 1).

The subject matter of EP 2386211 A1 (SYMRISE) is the use of rubusoside as well as of rubusoside-containing mixtures for masking, reducing or suppressing a bitter, acid and/or astringent taste impression ([0013]), whereby the mixtures mentioned are comprising one or more phenolic compounds in addition ([0019]).

In EP 2353403 A1 (SYMRISE) the use of deoxyhesperetin dihydrochalcone having a sweetening power is disclosed for influencing the intensity of taste impressions, to enhance the sweet taste impression of a sweet-tasting substance and to prevent or to mask an unpleasant taste impression of an unpleasantly tasting substance ([0024]).

The object of the present invention was therefore to provide novel substance mixtures which enhance, improve or perfect the sweet taste of oral preparations. In particular, an object of the present invention, on the one hand, consisted in perfecting the taste sensory profile of *Rubus* glycosides by a natural (enzymatic, fermentative or culinary) process, intending to obtain novel aroma compositions. A further object of the invention was to make accessible alpha-glycosyl rubusosides by natural processes, on the other. Besides perfecting the taste profile, the alpha-glycosyl rubusosides such obtained are characterised by their effectiveness in low concentrations and by the property of enhancing the sweet taste of other substances.

DESCRIPTION OF THE INVENTION

The subject matter of the invention is a substance mixture, comprising from 1% by weight to 60% by weight at least one compound following general formula (I) where m=n=0,

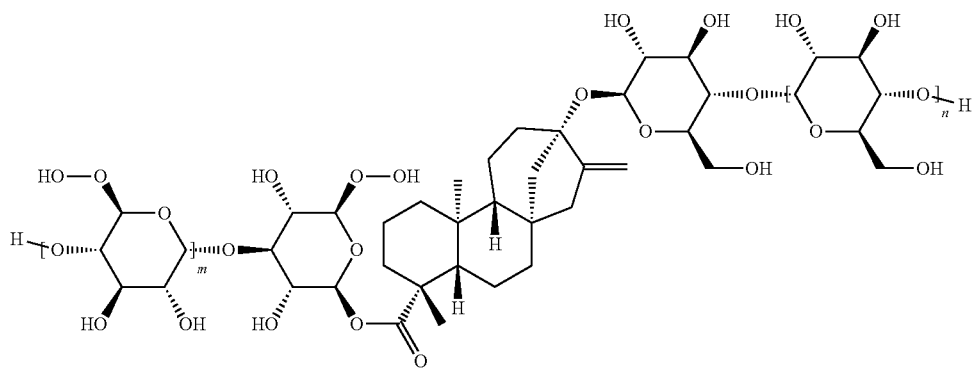

and at least one compound following general formula (I) where m or n≥1, with the proviso that m and n independently of one another represent 0 to 50.

Within the substance mixture according to the invention, the compounds following formula (I) preferably represent *Rubus* glycosides and/or alpha-glycosyl rubusosides.

*Rubus* Glycosides

*Rubus* glycosides may be obtained from the plant *Rubus suavissimus* S. Lee (Chinese blackberry), and consist of at least the diterpene glycoside rubusoside, preferably with a portion of from 1 to 100% by weight, particularly preferably of from 10 to 95% by weight, particularly preferably of from 30 to 75% by weight, each based on the total quantity of *Rubus* glycosides, and may comprise one or more of the 13 further isomers and homologues known to date such as suavioside A, B and R1, which, in part, however, also taste bitter (Hirono, S.; Chou, W. H.; Kasai, R.; Tanaka, O.; Tada, T., Sweet and bitter diterpene glucosides from leaves of *Rubus suavissimus*. Chemical & Pharmaceutical Bulletin 1990, 38, (6), 1743-1744 and Chou, G.; Xu, S.-J.; Liu, D.; Koh, G. Y.; Zhang, J.; Liu, Z., Quantitative and Fingerprint Analyses of Chinese Sweet Tea Plant (*Rubus suavissimus* S. Lee). *J. Agric Food Chem.* 2009, 57, 1076-1083.).

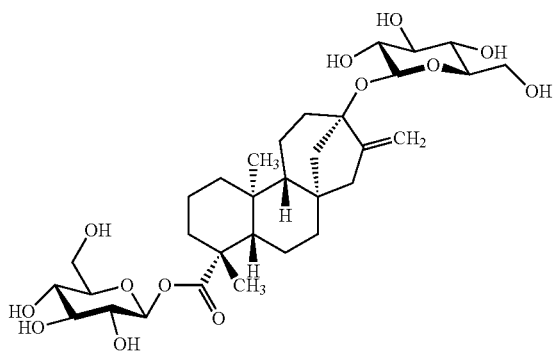

Rubusoside

The portions of the *Rubus* glycosides contained may differ depending on the cultivation area and the plant variety. The liquorice-like taste of the plant is counteracted by isolating the sweetening compounds and by subsequent composition during the production of the sweetener mixture. *Rubus* products usually have a portion of from 10%-70% rubusoside. Rubusoside itself may also be obtained by enzymatic conversion from steviosides as described in WO 2013/133689.

In the present invention, in contrast to the state of the art, the enzyme alpha-cyclodextringlucanotransferase (CGTase) is preferably used during the production of *Rubus* glycosides in the transglucosylation reaction with a 1,4-glycosidic carbohydrate, which is preferably starch. In doing so, it is possible to modify *Stevia* extracts, so that alpha-glycosyl steviosides are produced as described, e.g., in WO 2012/112180. This reaction has not been employed to produce *Rubus* extracts with an improved taste within the meaning of this invention. Accordingly, a further subject matter of the present invention is a process for the production of *Rubus* glycosides which are contained in a substance mixture according to the invention, comprising the use of alpha-cyclodextrin glucanotransferase in the transglucosylation reaction with a 1,4-glycosidic carbohydrate, which is preferably a carbohydrate.

Alpha-Glycosyl Rubusosides

Alpha-glycosyl rubusosides are enzymatically, fermentatively or chemically modified *Rubus* glycosides, particularly rubusosides following general formula (I), and have at least 1 to 20, preferably at least 2 to 10 and, particularly, 2 to 6 additional glucose units in addition to the two glucose units already contained in rubusoside (m=n=0), whereby these additional glucose units are preferably present as alpha-1, 4-linked D-glucopyranose units.

Surprisingly it was found that the substance mixtures according to the invention following general formula (I), in comparison with *Rubus* glycosides, do not solely have a significantly improved sweetening effect but are extremely suitable for improving, enhancing and optimising the initial sweetness and the mouthfeel of orally consumable preparations. In addition, an improved taste profile was exhibited, particularly with regard to the sweetening effect in comparison with compositions containing the substance mixture according to the invention, and compositions with a reduced portion in saccharose, or containing other sweet tasting carbohydrates. In particular, it was surprisingly shown that it was possible to reduce and/or mask the partially unpleasant sweetener-like aftertaste of the *Rubus* glycosides and/or alpha-glycosyl rubusosides with the substance mixture according to the invention in combination with phenolic sweet-enhancing aroma substances and also starch degradation products.

Accordingly, a preferred embodiment is a substance mixture according to the invention, comprising at least one compound following formula (I) where m=n=0 (=rubusoside).

Further, a substance mixture according to the invention in a preferred embodiment comprises at least one compound following formula (I) where m and n independently of one another are 0 to 50 and where the sum of m+n>0 and m+n≤50.

Accordingly, in a preferred embodiment a substance mixture according to the invention is present, which comprises at least one compound following formula (I) where m=n=0 and at least one further compound following formula (I) where m and n independently of one another represent 0 to 50 and where the sum of m+n>0 and m+n≤50.

In a further preferred embodiment of the present invention, a substance mixture according to the invention comprises additional starch degradation products in addition to at least one compound following formula (I) where m and n independently of one another represent 0 to 50, and where in case of m=n=0 at least one compound following general formula (I) where m or n≥1 is present. Starch degradation products, herein, are preferably starch degradation products containing from 3 to 100 alpha-1-4-linked D-glucopyranosyl groups each.

Starch Degradation Products

Suitable starch degradation products have the function of carrier substances in the mixtures according to the invention. Preference is given to dextrins or maltodextrins whose molecule size is between oligosaccharides and starch. Usually, they are present in the form of a white or a light yellow powder. They are mostly obtained from wheat, potato, tapioca or maize starch by dry heating (>150° C.) or under the exposure to acid. In nature, dextrin is, for example, produced by *Bacterium macerans*. Dextrins also develop by way of enzymatic degeneration of starch by amylase.

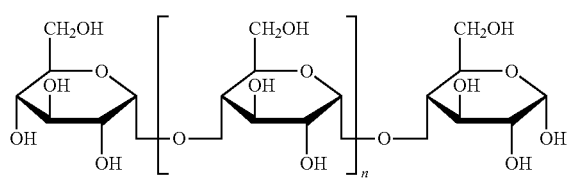

Maltodextrin

Maltodextrins, which are particularly suitable, have ca. 3 to ca. 20, preferably ca. 5 to ca. 15 dextrose equivalents (DE). This is understood to be the percentage of the reducing sugars in the dry matter.

In a further preferred embodiment of the present invention, a substance mixture according to the invention additionally comprises one or more phenolic, naturally occurring sweet-enhancing aroma substances selected from the group consisting of hesperetin, phloretin, 1-(2,4-Dihydroxyphenyl)-3-(3-hydroxy-4-methoxyphenyl)-propan-1-one, 7,3-Dihydroxy-4'methoxyflavane and 5-Hydroxy-4-(4-hydroxy-3-methoxyphenyl)-7-methoxy-2-chromanone.

In the substance mixture according to the invention, the compounds following formula (I) preferably represent *Rubus* glycosides, which are preferably rubusoside (m=n=0) or particularly preferably one of the alpha-glycosyl rubusosides following formula (II)

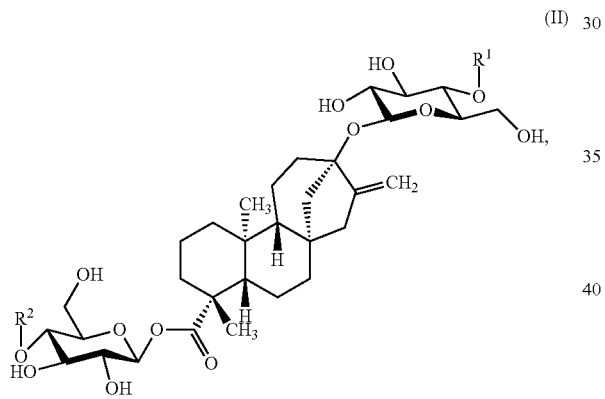

where the groups R1 and R2 represent the following groups:

| Compound | Rubus glycoside | $R^1$ | $R^2$ |
|---|---|---|---|
| 1 | Rubus triglucoside | H- | Glcα1- |
| 2 | Rubus triglucoside | Glcα1- | H- |
| 3 | Rubus tetraglucoside | Glcα1- | Glcα1- |
| 4 | Rubus tetraglucoside | -Glcα1-4Glcα | H- |
| 5 | Rubus tetraglucoside | H- | -Glcα1-4Glcα |
| 6 | Rubus pentaglucoside | -Glcα1-4Glcα | Glcα1- |
| 7 | Rubus pentaglucoside | Glcα1- | -Glcα1-4Glcα |
| 8 | Rubus hexaglucoside | -Glcα1-4Glcα | -Glcα1-4Glcα |
| 9 | Rubus pentaglucoside | -Glcα1-Glcα1-4Glcα | H- |
| 10 | Rubus pentaglucoside | H- | -Glcα1-4Glcα1-4Glcα |
| 11 | Rubus hexaglucoside | -Glcα1-Glcα1-4Glcα | Glcα1- |
| 12 | Rubus hexaglucoside | Glcα1- | -Glcα1-4 Glcα1-4 Glcα |
| 13 | Rubus heptaglucoside | -Glcα1-4Glcα | -Glcα1-Glcα1-4Glcα |
| 14 | Rubus heptaglucoside | -Glcα1-Glcα1-4Glcα | -Glcα1-4Glcα |
| 15 | Rubus octaglucoside | -Glcα1-Glcα1-4Glcα | -Glcα1-Glcα1-4Glcα |

Obviously, mixtures of compounds 1 to 15 and/or rubusoside are also possible and according to the invention. Accordingly, a preferred embodiment is a substance mixture with at least one compound following formula (I), which is selected from one of the compounds following formula (II):

*Rubus* triglucoside (compound 1),
*Rubus* triglucoside (compound 2),
*Rubus* tetraglucoside (compound 3),
*Rubus* tetraglucoside (compound 4),
*Rubus* tetraglucoside (compound 5),
*Rubus* pentaglucoside (compound 6),
*Rubus* pentaglucoside (compound 7),
*Rubus* hexaglucoside (compound 8),
*Rubus* pentaglucoside (compound 9),
*Rubus* pentaglucoside (compound 10),
*Rubus* hexaglucoside (compound 11),
*Rubus* hexaglucoside (compound 12),
*Rubus* heptaglucoside (compound 13),
*Rubus* heptaglucoside (compound 14),
*Rubus* octaglucoside (compound 15).

Preferably, the substance mixtures according to the invention comprise at least one compound following formula (I) (alpha-glycosyl rubusosides), where, preferably, the substance mixture according to the invention of the following composition is present:

(a1) 1% by weight to 60% by weight, preferably from 15% by weight to 50% by weight rubusoside (m+n=0), (a2) 1% by weight to 30% by weight, preferably from 5% by weight to 25% by weight alpha-glycosyl rubusosides with a total of 3 glucose units (m+n=1), (a3) 1% by weight bis 30% by weight, preferably from 5% by weight to 25% by weight alpha-glycosyl rubusosides with a total of 4 glucose units (m+n=2), (a4) 1% by weight to 25% by weight, preferably from 5% by weight to 20% by weight alpha-glycosyl rubusosides with a total of 5 glucose units (m+n=3), (a5) 0.1% by weight to 20% by weight, preferably from 1% by weight to 15% by weight alpha-glycosyl rubusosides with a total of 6 glucose units (m+n=4), (a6) 0.05% by weight to 10% by weight, preferably from 0.5% by weight to 5% by weight alpha-glycosyl rubusosides with a total of 5 glucose units (m+n=5), (a7) 0% by weight to 10% by weight, preferably 1% by weight to 8% by weight steviol monoside or its isomers, where one or more of the steviol monoside isomers are present in a ratio of from 100:1 bis 1:100 based on rubusoside, (a8) and 1% by weight to 90% by weight, preferably between 20% by weight and 80% by weight higher alpha-glycosyl rubusosides with 5 to up to 50 (m+n between 3 and 48), preferably 6 to 16 glycosidic units (m+n between 4 and 14), where the quantities of all components (a1) to (a8) together add up to at least 80% by weight, preferably at least 90% by weight. Here, the remaining quantity of 10 to 20% by weight is generally composed of water, glycerol, starch degradation products, proteins, fatty acids and/or fatty acid esters.

Particularly advantageous are substance mixtures according to the invention, comprising alpha-glycosyl rubusosides following formula I, having the following composition:
(a1) less than 50% by weight rubusoside (m+n=0),
(a2) more than 10% by weight alpha-glycosyl rubusosides with a total of 3 glucose units (m+n=1),
(a3) more than 15% by weight alpha-glycosyl rubusosides with a total of 4 glucose units (m+n=2),
(a4) more than 5% by weight alpha-glycosyl rubusosides with a total of 5 glucose units (m+n=3),
(a5) less than 6% by weight steviol monoside,
where the quantities of all components (a1) to (a5) together add up to at least 80% by weight, preferably at least 90% by weight. Here, the remaining quantity of 10 to 20% by weight is generally composed of water, glycerol, starch degradation products, proteins, fatty acids and/or fatty acid esters.

Very particularly preferably are substance mixtures according to the invention, particularly comprising alpha-glycosyl rubusosides following formula I, having the following composition:
(a1) less than 30% by weight rubusoside (m+n=0),
(a2) more than 15% by weight alpha-glycosyl rubusosides with a total of 3 glucose units (m+n=1),
(a3) more than 18% by weight alpha-glycosyl rubusosides with a total of 4 glucose units (m+n=2),
(a4) more than 10% by weight alpha-glycosyl rubusosides with a total of 5 glucose units (m+n=3),
(a5) less than 2.5% by weight steviol monoside,
where the quantities of all components (a1) to (a5) together add up to at least 80% by weight, preferably at least 90% by weight. Here, the remaining quantity of 10 to 20% by weight is generally composed of water, glycerol, starch degradation products, proteins, fatty acids and/or fatty acid esters.

Preferably, the substance mixtures according to the invention have a weight ratio of from 1:99 to 99:1, preferably of from 5:95 to 75:25, particularly preferably of from 25:75 to 75:25 and most preferably of from 5:95 to 25:75 between the component(s) of the compound(s) following formula (I) and the additional starch degradation product.

Accordingly, a preferred composition of a substance mixture according to the invention comprises, for example:
(a) 1% by weight to 99% by weight, preferably from 5% by weight to 50% by weight alpha-glycosyl rubusosides,
(b) 0.1% by weight to 15% by weight, preferably from 0.5% by weight to 10% by weight starch degradation products,
where the quantities of components (a) and (b) together add up to at least 80% by weight, preferably at least 90% by weight. Here, the remaining quantity of 10 to 20% by weight is generally composed of water, glycerol, starch degradation products, proteins, fatty acids and/or fatty acid esters.

In case of the substance mixtures which additionally contain a sweet-enhancing, naturally occurring phenolic aroma substance, the substance mixtures according to the invention have a weight ratio of from 1:99 to 99:1, preferably of from 10:90 to 90:10, particularly preferably of from 25:75 to 75:25 and most preferably of from 40:60 to 60:40 between the component(s) of the compound(s) following formula (I) and the additional starch degradation products (a+b) and the phenolic aroma substances (c).

Accordingly, a preferred composition of a substance mixture according to the invention comprises, for example:
(a) 20% by weight to 50% by weight, preferably from 27% by weight to 43% by weight alpha-glycosyl rubusosides,
(b) 0.1% by weight to 15% by weight, preferably from 0.5% by weight to 10% by weight maltodextrins, and
(c) 40% by weight to 60% by weight, preferably from 45% by weight to 55% by weight phenolic, naturally occurring sweet-enhancing aroma substances,
where the quantities of component (a), (b) and (c) together add up to at least 80% by weight, preferably at least 90% by weight. Here, The remaining quantity of 10 to 20% by weight is generally composed of water, glycerol, starch degradation products, proteins, fatty acids and/or fatty acid esters.

Production

The products according to the invention, comprising compounds following formula I (alpha-glycosyl rubusosides) are known in principle and may be produced, for example, according to Ohtani, K.; Aikawa, Y.; Ishikawa, H.; Kasai, R.; Kitahata, S.; Mizutani, K.; Doi, S.; Nakaura, M.; Tanaka, O., Further study on the 1,4-alpha-transglucosylation of rubusosides, a sweet steviol-bisglucoside from *Rubus suavissimus*. Agric. Biol. Chem. 1991, 55, (2), 449-453 by
i) mixing *Rubus* glycosides with an alpha-glucane, preferably starch, a starch degradation product or cyclodextrins with a glycoside hydrolase, preferably an alpha-glycosidase such as, for example, alpha-amylase, alpha-glucosidase, beta-amylase, cyclomaltodextrin glucanotransferase or a suitable microorganism which actively expresses such enzymes homologously or heterologously (e.g., *Xantomonas campestris, Saccharomyces cerevisiae* or *Leuconostoc mensenteroides*) at 0° C. to 90° C., preferably 5° C. to 80° C., particularly preferably 20° C. to 65° C., preferably in a water-containing medium for 0 to 48 hours, preferably 0.1 to 24 hours, particularly preferably 0.5-16 hours, and
ii) deactivating, pasteurising or sterilising the mixture obtained by heating it from 70° C. to 150° C. at normal or increased ambient pressure for 5 to 500 min, and
iii) subsequently drying the mixture obtained by means of, e.g., spray drying, freeze drying, distillative drying, belt drying, and
iv) optionally, further purifying the mixture by means of, e.g., chromatography, distribution processes, membrane processes or crystallisation.

Oral Preparations

A further subject matter of the present invention relates to preparations for oral ingestion which comprise the substance mixture(s) according to the invention and an quantity of from 0.00001% by weight to ca. 2% by weight. Preferably, the substance mixture(s) according to the invention are present in an quantity of from 0.0001% by weight to 1.5% by weight, particularly preferably from 0.001% by weight to 1% by weight, very particularly preferably from 0.01% by weight to 0.5% by weight and most particularly preferably from 0.05% by weight to 0.1% by weight.

Foodstuffs

The oral preparations in which the substance mixtures according to the invention may be used can be selected from the group consisting of
baked goods, for example, bread, dry biscuits, cakes, other baked products, confectionery (for example, chocolate, chocolate bar products, other bar products, fruit gum, hard and soft caramels, chewing gum), alcoholic or nonalcoholic beverages (for example, coffee, tea, iced tea, wine, wine-containing beverages, beer, beer-containing beverages, liqueurs, brandies, (carbonated) fruit-containing beverages, (carbonated) isotonic beverages, (carbonated) soft beverages, nectars, spritzers, fruit and vegetable juices, fruit or vegetable juice formulations, instant beverages (for example, instant cocoa beverages, instant tea beverages, instant coffee beverages, instant fruit beverages), meat products (for example, ham, fresh sausage or uncooked sausage formulations, seasoned or marinated fresh or salted meat products), eggs or egg products (dried egg, egg white, egg yolk), cereal products (for example, breakfast cereals, muesli bars, precooked ready-made rice products), dairy products (for example, milk beverages, buttermilk beverages, milk ice, yoghurt, kefir, fresh cheese, soft cheese, hard cheese, dried milk powder, whey, whey beverages, butter, buttermilk, products containing partly or completely hydrolysed milk protein), products made of soy protein or other soybean fractions (for example, soy milk and products produced thereof, fruit beverages with soy protein, soy lecithin-containing formulations, fermented products such as tofu or tempe or products produced thereof), products made of other plant-based protein sources, for example, oat protein beverages fruit preparations (for example, preserves, fruit ice-cream, fruit sauces, fruit fillings), vegetable preparations (for example, ketchup, sauces, dried vegetables, frozen vegetables, precooked vegetables, vegetables preserved in vinegar), snacks (for example, baked or fried potato chips (crisps) or potato dough products, extrudates based on maize or peanuts), fat- and oil-based products or emulsions thereof (for example, mayonnaise, remoulade, dressings), other ready-made dishes and soups (for example dried soups, instant soups, precooked soups), spices or spice formulations and particularly seasonings, which are used, for example, in the snacks sector.

Particularly preferred herein are sweets, dairy products and very particularly preferred are non-alcoholic beverages where sweetened beverages are particularly preferred.

Additives and Adjuvants

The oral preparations and foodstuffs mentioned above may typically contain further additives and adjuvants, particularly including sweeteners, food acids, acid regulators, thickeners and particularly further aroma substances.

A1. Sweeteners

Suitable sweeteners or sweet tasting additives are, firstly, carbohydrates and specifically sugars such as, for example, sucrose/saccharose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde or maltodextrin. Plant-based preparations containing these substances are also suitable, for example, on the basis of sugarbeet (*Beta vulgaris* ssp., sugar fractions, sugar syrup, molasses), sugar cane (*Saccharum officinarum* ssp., molasses, sugar cane syrup), maple syrup (*Acer* ssp.) or agave (agave syrup).

Suitable are also synthetic, i.e. usually enzymatically produced starch or sugar hydrolysates (invert sugar, fructose syrup);

fruit concentrates (e.g., on the basis of apples or pears);

sugar alcohols (e.g., erythritol, threitol, arabitol, ribotol, xylitol, sorbitol, mannitol, dulcitol, lactitol);

proteins (e.g., miraculin, monellin, thaumatin, curculin, brazzein);

sweeteners (e.g., magap, sodium cyclamate, acesulfam K, neohesperidin dihydrochalcone, saccharine sodium salt, aspartame, superaspartame, neotame, alitame, sucralose, stevioside, rebaudioside, lugduname, carrelame, sucrononate, sucrooctate, monatin, phenylodulcin);

sweet-tasting amino acids (e.g., glycine, D-leucine, D-threonine, D-asparagine, D-phenylalanine, D-tryptophan, L-proline);

further sweet-tasting low-molecular substances such as, e.g., hernandulcin, dihydrochalcon glycoside, particularly, neohesperidin dihydrochalcone, and naringin chalcone, glycyrrhizin, glycerrhetinic acid, their derivatives and salts, extracts of liquorice (*Glycyrrhizza glabra* ssp.), *Lippia dulcis* extracts, *Momordica* ssp. extracts or individual substances such as, for example, *Momordica grosvenori* [Luo Han Guo] and the mogrosides obtained thereof, *Hydrangea dulcis* or extracts, phyllodulcin or balansins of *Mycetia balansae* as described in WO 2012/164062.

A2. Food Acids

Suitable food acids are carboxyclic acids. Acids within the meaning of the invention are preferably acids approved for use in foods, particularly the ones mentioned here:

E260—Acetic acid
E270—Lactic acid
E290—Carbon dioxide
E296—Malic acid
E297—Fumaric acid
E330—Citric acid
E331—Sodium citrates
E332—Potassium citrates
E333—Calcium citrates
E334—Tartaric acid
E335—Sodium tartrates
E336—Potassium tartrates
E337—Sodium potassium tartrate
E338—Phosphoric acid
E353—Metatartaric acid
E354—Calcium tartrate
E355—Adipic acid
E363—Succinic acid
E380—Triammonium citrate
E513—Sulphuric acid
E574—Gluconic acid
E575—Glucono delta-lactone A3. Acidity Regulators Acidity regulators are food additives which maintain the degree of acidity or alkalinity and, thus, the desired pH value of a food on a constant level. They are mostly organic acids and their salts, carbonates, and only rarely inorganic acids and their salts. The addition of an acidity regulator partly enhances the stability and firmness of the food and improves the effect of preservatives. In contrast to acidifiers, they are not used to change the taste of foods. Their effect is based on the formation of a buffer system within the food, which is cabable of balancing acids and bases such that the pH value is not, or only slightly, changed. Examples are:

E170—Calcium carbonate
E260-263—Acidic acid and acetates
E270—Lactic acid
E296—Malic acid
E297—Fumaric acid
E325-327—Lactates (Lactic acid)
E330-333—Citric acid and and citrates
E334-337—Tartaric acid and tartrates
E339-341—Orthophosphate
E350-352—Malates (Malic acid)
E450-452—Di-, Tri- and Polyphosphates
E500-504—Carbonates (Carbonic acid)
E507—Hydrochloric acid and chlorides
E513-517—Sulphuric acid and sulphates
E524-528—Hydroxides
E529-530—Oxides
E355-357—Adipic acid and adipates
E574-578—Gluconic acid and gluconates A4. Thickeners Thickeners are substances which, primarily, are capable of binding water. Removing unbound water leads to an increase in viscosity. Cross-linking effects occur together with this effect starting with a concentration that is characteristic for each thickener, which lead to a mostly overproportional increase in viscosity. In this case, this is referred to as a "communication" of the molecules, i.e., an entanglement. Most thickeners are linear or branched makromolecules (e.g., polysaccharides or proteins) which may interact by way of intermolecular interactions such as hydrogen bonds, hydrophobic interactions or ionic relationships. Extreme cases of thickeners are layered silicates (bentonite, hectorite) or hydrated $SiO_2$ particles, which are dispersed and present as particles, and may bind water in their solid-like structure, or may interact with one another due to the described interactions. Examples are:

E400—Alginic acid
E401—Sodium alginate
E402—Potassium alginate
E403—Ammonium alginate
E404—Calcium alginate
E405—Propylene glycol alginate
E406—Agar
E407—Carrageenan, Furcellaran
E410—Locust bean gum
E412—Guar gum
E413—Tragacanth
E414—Gum arabic
E415—Xanthan gum
E416—Karaya gum (Indian Gum Tragacanth)
E417—Tara gum (Peruvian locust bean gum)
E418—Gellan gum
E440—Pectins, Opekta
E440ii—Amididated pectin
E460—Microcrystalline cellulose, cellulose powder
E461—Methyl cellulose
E462—Ethyl cellulose
E463—Hydroxypropyl cellulose
E465—Ethyl methyl cellulose
E466—Carboxymethyl cellulose, sodium carboxymethyl cellulose A6. Aroma Substances Aroma substances. The oral preparations according to the invention may contain one or more aroma substances. Typical examples comprise: acetophenone, allyl caproate, alpha-ionone, beta-ionone, aniseed aldehyde, anisyl acetate, anisyl formate, benzaldehyde, benzothiazole, benzyl acetate, benzyl alcohol, benzyl benzoate, beta-ionone, butyl butyrate, butyl capronate, butylidene phthalide, carvone, camphene, caryophyllene, cineol, cinnamyl acetate, citral, citronellol, citronellal, citronellyl acetate, cyclohexyl acetate, cymol, damascone, decalactone, dihydrocoumarin, dimethyl anthranilate, dimethyl anthranilate, dodecalactone, ethoxy ethyl acetate, ethylbutyric acid, ethyl butyrate, ethyl caprinate, ethyl capronate, ethyl crotonate, ethyl furaneol, ethylguaiakol, ethyl isobutyrate, ethyl isovalerianate, ethyl lactate, ethylmethyl butyrate, ethyl propionate, eucalyptol, eugenol, eugenyl acetate, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g., 5 Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formiate, cis-2-hexyl acetate, cis-3-hexyl acetate, trans-2-hexyl acetate, cis-3-hexyl formiate, para-hydroxybenzyl acetone, isoamyl alcohol, isoamyl isovalerianate, isobutyl butyrate, isobutyl aldehyde, isoeugenol methyl ether, isopropyl methyl thiazole, lauric acid, levulinic acid, linalool, linalool oxide, linalyl acetate, menthol, menthofuran, methyl anthranilate, methyl butanol, methyl butyric acid, 2-methyl butyl acetate, methyl capronate, methyl cinnamate, 5-methyl furfural, 3,2,2-methyl cyclopentenolone, 6,5,2-methyl heptenone, methyl dihydrojasmonate, methyljasmonate, 2-methyl methylbutyrate, 2-methyl-2-pentanoic acid, methyl thiobutyrate, 3,1-methyl thiohexanol, 3-methyl thiohexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentandione, phenylethyl acetate, phenylethyl alcohol, phenylethyl alcohol, phenylethyl isovalerianate, piperonal, propionaldehyde, propyl butyrate, pulegon, pulegol, sinensal, sulfurol, terpinene, terpineol, terpinolene, 8,3-thiomenthanone, 4,4,2-thiomethyl pentanone, thymol, delta-undecalactone, gamma-undecalactone, valencene, valeric acid, vanilline, acetoine, ethyl vanilline, ethyl vanilline isobutyrate (=3-ethoxy-4-isobutyryloxybenzaldehyde), 2,5-dimethyl-4-hydroxy-3 (2H)-furanone and derivatives (here, preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here, preferably ethyl maltol), coumarine and coumarine derivatives, gamma-lactones (here, preferably gamma-undecalactone, gamma-nonalactone, gamma-decalactone), delta-lactones (here, preferably 4-methyldeltadecalactone, massoilactone, delta-decalactone, tubero lactone), methyl sorbate, divanilline, 4-hydroxy-2(or 5)-ethyl-5(or 2)-methyl-3(2H)furanone, 2-hydroxy-3-methyl-2-cyclopentenon, 3-hydroxy-4,5-dimethyl-2(5H)-furanone, isoamyl acetate, ethyl butyrate, butyl butyrate, isoamyl butyrate, methyl-3-ethyl butyrate, n-hexanoic acid allyl ester, n-hexanoic acid-n-butyl ester, n-ethyl octanoate, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furane, 2-methyl-3-furanthiol, bis(2-methyl-3-furyl)disulfide, furfuryl mercaptane, methional, 2-acetyl-2-thiazoline, 3-mercapto-2-pentanone, 2,5-dimethyl-3-furanthiol, 2,4,5-trimethylthiazol, 2-acetylthiazol, 2,4-dimethyl-5-ethylthiazol, 2-acetyl-1-pyrroline, 2-methyl-3-ethylpyrazine, 2-ethyl-3,5-dimethylpyrazine, 2-ethyl-3,6- dimethylpyrazine, 2,3-diethyl-5-methylpyrazine, 3-isopropyl-2-methoxypyrazine, 3-Isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-Penten-3-one, 4-hydroxy-2,5-dimethyl-3(2H)-furanone, guaiakol, 3-hydroxy-4,5-dimethyl-2(5H)-furanone, 3-hydroxy-4-methyl-5-ethyl-2(5H)-furanone, cinnamon aldehyde, cinnamon alcohol, methyl salicylate, isopulegol and (not explicitly mentioned here) stereoisomers, enantiomers, positional isomers, diastereomers, cis/trans-isomers and epimers of these substances.

Aroma substances conveying both a milky-creamy taste impression and providing mouthfulness (such as, e.g., diacetyl, acetoin or delta-lactone) are particularly highlighted, as are aroma substances conveying a sweet-caramellike taste impression, which supports a sugar profile (such as, e.g., maltol, vanilline, benzaldehyde, furaneol, heliotropin).

A7. Aroma Substances for Masking Unpleasant Taste Impressions

Further, the above mentioned oral preparations and foodstuffs according to the invention may predominantly comprise additional aroma substances which may reduce or suppress, an unpleasant (bitter, astringent, dry, floury, metallic, chalky) impression or aftertaste of the preparations, the so-called taste correctors. These taste correctors are, for example, selected from the following list: lactisoles, lactisol esters such as described in EP 2,292,224, sodium salts (e.g., sodium chloride, sodium lactate, sodium nitrate, sodium acetate, sodium gluconate), hydroxyflavanones, here, preferably eriodictyol, sterubin (eriodictyol-7-methyl ether), homoeriodictyol, and their sodium, potassium, calcium, magnesium or zinc salts (particularly those as described in EP 1258200 A2, which is incorporated into this application by way of reference with regard to the corresponding compounds disclosed therein), divanillins (particularly those as described in WO 2004/078302 which is incorporated into this application by way of reference with regard to the corresponding compounds disclosed therein) and 4-hydroxydihydrochalcones (preferably as described in U.S. Pat No. 2008/0227867 A1 which is incorporated into this application by way of reference with regard to the corresponding compounds disclosed therein), here, particularly phloretin and davidigenin, umami aromas as described in WO 2008/046895 A1 and EP 1989944 A1, umami compounds as described in EP 2064959 A1, EP 2,529,632 B1 or EP 2135516 A1, here particularly preferably rubemamine and rubescenamine, vanillyl lignans, particularly preferably lariciresinol or matairesinol as described in WO 2012/146584, enterodiol as described in DE 10 2012 214 560, alkamides, particularly pellitorines as described in EP 2,058,297, EP 1,977,655 B1 and EP 2,008,530 B1, and N-decadienoyl amino acids as described in EP 2,597,082 and their mixtures.

Oral and Tooth Care Products

In a preferred embodiment, the oral preparations may be selected from the group consisting of mouth and tooth care agents, which also include mouth washs and chewing gums.

Specific examples thereof are toothpastes, tooth gels, tooth powders, mouth washs and the like. In general, tooth pastes and tooth cremes are generally understood to be gel or pasty compositions of water, thickeners, moisturizers, abrasives or cleaning agents, surfactants, sweeteners, aroma substances, deodorizing agents and agents against oral and dental conditions. Tooth pastes according to the invention may comprise any common cleaning agents such as, for example, chalk, dicalcium phosphate, insoluble sodium metaphosphate, aluminium silicates, calcium pyrophosphate, fine-particle synthetic resins, silicic acids, aluminium oxide and aluminiumoxide trihydrate.

Particularly suitable cleaning agents for the tooth pastes according to the invention are, preferably, fine-particle silicic acid xerogels, silicic acid hydrogels, precipitation silicic acids, aluminiumoxide trihydrate and fine-particle alphaaluminiumoxide or mixtures of said cleaning agents in quantities of 15 to 40% by weight of the tooth paste. Suitable moisturizers are, preferably, low-molecular polyethylene glycols, glycerol, sorbit or mixtures of these products in quantities of up to 50% by weight. Suitable known thickeners are the thickening, fine-particle gel silicic acids and hydrocolloids such as, for example, carboxymethyl cellulose, hydroxyethyl cellulose, hydroxypropyl guar, hydroxyethyl starch, polyvinyl pyrrolidone, high-molecular polyethylene glycol, vegetable gums such as gum tragacanth, agar-agar, carrageen moss, gum arabic, xanthan gum and carboxyvinyl polymers (for example, Carbopol® types). In addition to the mixtures of menthofuran and menthol compounds, the oral and dental care products may comprise, in particular, surface-active substances, preferably, anionic and nonionic high-foam surfactants such as the substances mentioned above, particularly, alkylether sulphate salts, alkyl polyglucosides and their mixtures.

Further common additives to tooth pastes are:
preservatives and anti-microbial agents such as, for example, p-hydroxybenzoic acid methyl/ethyl or propyl esters, sodium sorbate, sodium benzoate, bromochlorophene, phenyl salicylic acid esters, thymol and the like;
anti-calculus agents, such as organophosphates, for example, 1-hydroxyethane-1,1-diphosphonic acid, 1-phosphonopropane-1,2,3-tricarboxyfic acid and others, which are known for example, from U.S. Pat. No. 3,488,419, DE 2224430 A1 and DE 2343196 A1;
other anti-cariogenic substances such as, for example, sodium fluoride, sodium monofluorophosphate, tin fluoride;
sweeteners such as, for example, saccharin sodium, sodium cyclamate, sucrose, lactose, maltose, fructose or Apartame®, (L-Aspartyl-L-phenylalanin-methylester), *Stevia* extracts or their sweetening compounds, particularly, rebaudiosides;
additional aromas such as, for example, *eucalyptus* oil, aniseed oil, fennel oil, caraway oil, methyl acetate, cinnamon aldehyde, anethole, vanillin, thymol and mixtures of these and other natural and synthetic aromas;
pigments such as, for example, titanium dioxide;
colourants;
buffer substances such as, for example, primary, secondary or tertiary alkali phosphates or citric acid/sodium citrate;
wound-healing and inflammation-inhibiting substances such as, for example, allantoin, urea, azulene, chamomile active ingredients and derivatives of acetylsalicylic acid.

A preferred embodiment of the cosmetic preparations are tooth pastes in form of an aqueous, pasty dispersion, comprising polishing agents, moisturizers, viscosity regulators and, optionally, further common components, as well as the mixture of menthofurane and menthol compounds in quantities from 0.5 to 2% by weight.

For mouthwashs, a combination with hydroalcoholic solutions of differing degrees of essential oils, emulsifiers, astringent and toning drug extracts, calculus-inhibiting agents, anti-bacterial additives and flavour correctants is quite possible. Another preferred embodiment of the invention is a mouthwash in form of an aqueous or a hydroalcoholic solution, comprising the mixture of menthofuran and menthol compounds in quantities of from 0.5 to 2% by weight. In mouthwash compositions, which are thinned before application, higher concentrations may yield sufficient effects corresponding to the intended thinning ratio.

In addition, hydrotropes, for example, ethanol, isopropyl alcohol or polyols, may be used to improve flow behavior; these substances broadly correspond with the carriers described at the beginning. Suitable polyols, preferably, contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example, sorbitol or mannitol,
sugars containing 5 to 12 carbon atoms, for example, glucose or sucrose;
amino sugars, for example, glucamine;
dialcoholamines, such as diethanolamine or 2-aminopropane-1,3-diol.

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are, for example, mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are, for example, benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Chewing Gums

As far as the oral preparations are chewing gums, these typically contain a water-insoluble and a water-soluble component.

The water-insoluble base, which is also known as "gum base", typically comprises natural or synthetic elastomers, resins, fats and oils, plasticizers and softeners, fillers, colourants and optionally waxes. The base normally makes up 5 to 95% by weight, preferably 10 to 50% by weight, and more particularly 20 to 35% by weight of the composition as a whole. In a typical form of embodiment of the invention, the base consists of 20 to 60% by weight synthetic elastomers, 0 to 30% by weight natural elastomers, 5 to 55% by weight plasticizers, 4 to 35% by weight fillers, and small quantities of additives such as colourants, antioxidants and the like, with the proviso that they are soluble in water in small quantities at best.

Suitable synthetic elastomers are, for example, polyisobutylenes with average molecular weights (as measured by GPC) of 10,000 to 100,000 and preferably 50,000 to 80,000, isobutylen/isoprene copolymers ("butyl elastomers"), styrene/butadiene copolymers (styrene:butadiene ratio, for example, 1:3 to 3:1), polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers such as, for example, smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether bubbles are to be produced with the chewing gums ("bubble gums") or not. Elastomer mixtures containing jelutong, chicle, sorva and massanduraba are preferably used.

In most cases, the elastomers are too hard or lack plasticity for satisfactory processing, so it has been found to be of advantage to use special plasticizers which, of course, must also satisfy in particular all requirements relating to acceptability as food additives. In this respect, suitable plasticizers are, above all, esters of resin acids, for example, esters of lower aliphatic alcohols or polyols with completely or partly hydrogenated, monomeric or oligomeric resin acids. In particular, the methyl, glycerol or pentaerythritol esters or mixtures thereof are used for this purpose. Alternatively, terpene resins, which may be derived from α-pinene, β-pinene, δ-limonene or mixtures thereof, could also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable colourants and whiteners are, for example, the FD & C types, plant and fruit extracts permitted for colouring foods and titanium dioxide.

The gum bases may contain waxes, or may be wax-free; examples of wax-free compositions can be found inter alia in U.S. Pat. No. 5,286,500, to the disclosure of which reference is hereby specifically made.

In addition to the water-insoluble gum base, chewing gum compositions regularly contain a water-soluble component, which is formed, for example, by softeners, sweeteners, fillers, flavours, flavour enhancers, emulsifiers, colourants, acidifiers, antioxidants and the like, with the proviso in this case that the constituents have at least adequate solubility in water. Accordingly, individual constituents may belong both to the water-insoluble phase and to the water-soluble phase, depending on the water solubility of the special representatives. However, combinations may also be used, for example, a combination of a water-soluble and a water-insoluble emulsifier, in which case the indivival representatives are present in different phases. The water-insoluble component usually makes up 5 to 95% by weight and preferably 20 to 80% by weight of the preparation.

Water-soluble softeners or plasticizers are added to the chewing gum compositions to improve chewability and the chewing feel and are present in the mixtures in quantities of typically 0.5 to 15% by weight. Typical examples are glycerol, lecithin and aqueous solutions of sorbitol, hydrogenated starch hydrolysates or corn syrup.

Suitable sweeteners are both sugar-containing or sugar-free compounds which are used in quantities of 5 to 95% by weight, preferably in quantities of 20 to 80% b weight and more particularly in quantities of 30 to 60% by weight, based on the chewing gum composition. Typical saccharide sweeteners are sucrose, dextrose, maltose, dextrin, dried invert sugar, fructose, fructose, levulose, galactose, corn syrup and mixtures thereof. Suitable sugar substitutes are sorbitol, mannitol, xylitol, hydrogenated strarch hydrolysates, maltitol and mixtures thereof. Further suitable additives are so-called high-intensity artificial sweeteners (HIAS) such as, for example, sucralose, aspartame, acesulfam salts, alitam, saccharin and saccharin salts, cyclamic acid and salts thereof, glycyrrhicins, dihydrochalcones, thaumatin, monellin and the like either individually or in the form of mixtures.

Fillers are particularly suitable for the production of low-calorie chewing gums and may be selected, for example, from polydextrose, raftilose, raftilin, fructo-oligosaccharides (NutraFlora), palatinose oligosaaccharides, guar gum hydrolysates (Sun Fiber) and dextrins.

The choice of other flavours is virtually unlimited and is not critical to the essence of the invention. All flavours normally make up from 0.1 to 15% by weight and, preferably, from 0.2 to 5% by weight of the chewing gum composition. Suitable flavours are, for example, essential oils, synthetic aromas and the like, such as, for example, aniseed oil, Japanese anise oil, caraway oil, eucalyptus oil, fennel oil, citrus oil, wintergreen oil, clove oil, menthol and the like, such as used, for example, in oral and dental care products.

The chewing gums may additionally contain auxiliaries and additives, which are suitable, for example, for dental care, more particularly for controlling plaque and gingivitis, such as, for example, chlorhexidine, CPC or triclosan. They may also contain pH adjusters (for example, buffer or urea), anti-caries agents (for example, phosphates or fluorides), biogenic agents (antibodies, enzymes, caffeine, plant extracts), providing these substances are permitted in foods and do not undesirably interact with one another.

INDUSTRIAL APPLICABILITY

A further subject matter of the present invention is the use of the substance mixture according to the invention for the production of aroma compositions. The aroma compositions so produced are particularly advantageous, particularly for use in improving, enhancing or conveying a sweet taste and/or for masking an unpleasant taste impression, for example, of sweeteners, preferably selected from bitter, astringent and/or sweetener-like (after)taste.

Accordingly, a further subject matter of the present invention is the use of the substance mixtures according to the invention for improving, enhancing or conveying the sweet taste and/or for masking an unpleasant taste impression, for example, of sweeteners, preferably selected from bitter, astringent and/or sweetener-like (after)taste.

In addition, therefore, a subject matter of the invention is an aroma composition, comprising substance mixtures described above.

Particularly, the invention relates to an orally consumable preparation, comprising a substance mixture according to the invention or an aroma composition according to the invention, which comprise the substance mixtures according to the invention.

Further, the invention relates to a process for improving, enhancing or conveying a sweet taste or for masking unpleasant taste impressions, selected from bitter, astringent and/or sweetener-like (after) taste, comprising the steps of:
  a) providing a sweetener which causes an unpleasant taste impression in the oral region,
  b) providing a substance mixture according to the instant disclosure,
  c) mixing the components of step a) and b).

Further subject matters of the present invention are, on the one hand, directed to a process for taste optimization of preparations for oral uptake, characterized in that these are added from 0.0001% by weight to 2% by weight of the mixtures, comprising the components
  (a) *Rubus* glycosides and/or alpha-glycosyl rubusosides, and
  (b) starch degradation products, and
  (c) optionally, one or more phenolic, naturally occurring sweet-enhancing aroma substances, selected from the group consisting of hesperetin, phloretin, 1-(2,4-Dihydroxyphenyl)-3-(3-hydroxy-4-methoxyphenyl)-propan-1-one, 7,3-Dihydroxy-4'methoxyflavane and 5-Hydroxy-4-(4-hydroxy-3-methoxy-phenyl)-7-methoxy-2-chromanone.

Finally, the invention relates to the use of the substance mixtures containing the components (a) *Rubus* glycosides and/or alpha-glycosyl rubusosides, and (b) starch degradation products, and (c) optionally, one or more phenolic, naturally occurring sweet-enhancing aroma substances, selected from the group consisting of hesperetin, phloretin, 1-(2,4-Dihydroxyphenyl)-3-(3-hydroxy-4-methoxyphenyl)-propan-1-one, 7,3-Dihydroxy-4'methoxyflavane and 5-Hydroxy-4-(4-hydroxy-3-methoxy-phenyl)-7-methoxy-2-chromanone as aroma compositions for preparations for oral uptake.

With regard to the preferred preparations of the mixtures, the preferred used or added quantities and the nature of the aroma substances it is referred to the above explanations.

A further subject matter of the present invention is a process for improving, enhancing or conveying the sweet taste or for masking unpleasant taste impressions, selected from bitter, astringent and/or sweetener-like (after) taste, comprising the steps:

(a) providing a sweetener which causes an unpleasant taste impression in the oral area, (b) providing a substance mixtures according to the instant disclosure, (c) mixing the components of step a) and b).

EXAMPLES

Example 1

Formulation Example of Alpha-Glycosyl Rubusosides

Maltodextrin DE 17-20 from potato and blackberry leaf extract, containing 70% rubusoside are weighed in the ratio of 1:1. The mixture is stirred while adding 0.1 M sodium phosphate buffer, pH 7 until all components are completely dissolved. The reaction is started by adding 1,4 KNU-CP cyclomaltodextrin glucanotransferase per gramme of substrate. The mixture is subsequently incubated for 15 h at 50° C. with light shaking for 10 min, is heated to 80° C. and then freeze-dried. The analysis of the mixture was completed by means of LC-MS and AF4.

Example 2

Aroma Compositions

The components stated below are blended to yield the corresponding aroma compositions.

TABLE 2

| Aroma compositions (indications in % by weight) | | | | | | | | | | |
|---|---|---|---|---|---|---|---|---|---|---|
| Composition | A | B | C | D | E | F | G | H | I | J |
| Substance mixture A containing maltodextrins of example 1 | 10 | 20 | 10 | | | 10 | | 10 | | |
| Substance mixture E containing maltodextrins of example 1 | | | | 20 | 15 | | 7.5 | | | |
| Substance mixture F example 1 | | | | | | | | | 20 | |
| Substance mixture 1 example 1 | | | | | | | | | | 20 |
| Glycerol | 10 | 20 | | 30 | | 20 | 15 | 30 | 10 | 20 |
| Gum arabic solution (20%) | | | | | | | | 10 | | |
| 1,2-propylene glycol | | | | | Ad 100 | | | | | |

Example 3

Beverage Formulation

Various substance mixtures according to the invention were used for the production of simple soft beverages and the products were stored for 48 h at 20° C. Subsequently, the taste properties (descriptors: initial sweetness, intensity of sweetness, sugar taste/mouthfulness) were evaluated by a panel consisting of 8 trained testers on a linear scale of from 0 (not present) to 10 (strongly expressed). The compositions and results are summarised in the following Table 3. The embodiments 1 and 2 are according to the invention, examples V1, V2 and V3 serve comparison purposes. Example C corresponds to the standard, i. e. to the taste evaluation of the product without the addition of aroma.

TABLE 1

Composition of substance mixtures for aroma compositions, containig alpha-glycosyl rubusosides and starch degradation products (indication in area %)

| Component | A | B | C | D | E | F | G | H | I | J | K | L |
|---|---|---|---|---|---|---|---|---|---|---|---|---|
| Steviol monoside | 2.3 | 2.1 | 1.4 | 1.9 | 1.8 | 1.9 | 1.4 | 5.6 | 1.6 | 2.4 | 2.8 | 1.6 |
| Rubusoside | 15.1 | 20.4 | 13.9 | 16.2 | 16.9 | 19.2 | 15.7 | 20.1 | 18.1 | 23.2 | 28.3 | 17.9 |
| Rubus triglucoside | 13.5 | 18.0 | 14.6 | 15.9 | 15.5 | 17.1 | 15.8 | 17.7 | 17.2 | 18.0 | 21.7 | 16.7 |
| Rubus tetraglucoside | 20.4 | 23.6 | 18.2 | 18.8 | 18.5 | 19.1 | 14.9 | 19.5 | 22.2 | 21.1 | 21.9 | 18.1 |
| Rubus pentaglucoside | 13.1 | 11.6 | 18.9 | 17.6 | 17.8 | 15.9 | 17.9 | 15.7 | 16.3 | 15.3 | 10.0 | 16.0 |
| Rubus hexaglucoside | 9.3 | 5.1 | 10.3 | 9.6 | 9.7 | 8.5 | 9.8 | 8.2 | 7.8 | 7.0 | 3.0 | 8.8 |
| Rubus heptaglucoside | 2.8 | 1.9 | 5.2 | 4.8 | 4.9 | 4.0 | 4.9 | 3.6 | 3.6 | 3.2 | 0.9 | 3.7 |
| Starch degradation products | 4.5 | 6.1 | 4.9 | 6.4 | 6.1 | 6.6 | 1.9 | 5.5 | 4.2 | 3.3 | 4.6 | 7.6 |
| Sum | 81.0 | 88.8 | 87.4 | 91.2 | 91.2 | 9.23 | 82.3 | 95.9 | 91 | 93.5 | 93.2 | 90.4 |

TABLE 3

Taste properties of soft drink formulations (indications in % by weight)

| Composition | C | 1 | 2 | V1 | V2 | V3 |
|---|---|---|---|---|---|---|
| Sucrose | 7 | 7 | 7 | 7 | 7 | 7 |
| Citric acid | 0.15 | 0.15 | 0.15 | 0.15 | 0.15 | 0.15 |
| Substance mixture A containing maltodextrins of example 1 | — | 0.01 | 0.01 | — | — | — |
| Hesperetin | — | — | 0.00075 | 0.00075 | — | 0.00075 |
| Blackberry leaf extract containing 70% rubusoside | — | — | — | — | 0.005 | 0.005 |
| Maltodextrin | — | — | — | — | 0.005 | 0.005 |
| Water | | | | Ad 100 | | |
| Initial sweetness | 3.4 | 5.5 | 5.6 | 3.5 | 4.5 | 5.0 |
| Intensity of sweetness | 3.6 | 5.9 | 6.4 | 3.9 | 4.9 | 5.4 |
| Sugar taste and mouthfulness | 3.3 | 5.1 | 5.9 | 3.6 | 4.5 | 5.1 |
| Persistent sweet taste, sweetener-likeness | 2.1 | 3.1 | 2.8 | 2.1 | 2.7 | 3.3 |

The sugar-reduced control sample C clearly received the worst evaluations, sample 2, in contrast, the best. Here, the addition of small quantities of hesperetin (V1) does not improve the taste results. The two embodiments according to the invention 1 and 2 exhibit an improved initial sweetness, increased intensity of sweetness and an improved sugar taste/mouthfulness in comparison with the sugar variant (C). Here, embodiment 1 exhibits a higher intensity of sweetness and initial sweetness as well as an improved mouthfulness in comparison with sample V2. The combination of alpha-glycosyl rubusosides with (2), on the one hand, leads to a further increase in the intensity of sweetness and mouthfulness in comparison with the variant having alpha-glycosyl rubusosides alone (1) and the variant having rubusoside and hesperetin (V3). On the other hand, the combination of hesperetin with alpha-glycosyl rubusosides in the embodiment of the invention (2) leads to a masking of the sweetener-likeness or the liquorice-like aftertaste in comparison to the combination of rubusoside with hesperetin (V3).

Examples 4 to 9

In the following, the invention is illustrated by means of further formulation examples:

Example 4

Soft beverages (indications in % by weight)

| Ingredients | A | B | C | D | E | F | G |
|---|---|---|---|---|---|---|---|
| Sucrose | 10 | 10 | 7 | — | — | 8 | 7 |
| Glucose/fructose syrup | — | — | — | — | 10 | — | — |
| Substance mixture B containing maltodextrins of example 1 | 0.01 | 0.015 | 0.005 | 0.02 | 0.01 | 0.005 | 0.002 |
| Citric acid | 0.15 | 0.15 | 0.06 | 0.15 | 0.15 | 0.15 | 0.15 |
| Phosphoric acid | — | — | 0.07 | — | — | — | — |
| Caramel | — | — | 0.14 | — | — | — | — |
| Caffeine | — | — | 0.01 | — | — | — | — |
| Citrus aroma | 0.1 | 0.05 | — | 0.1 | 0.1 | 0.1 | 0.1 |
| Lemon aroma | — | 0.05 | — | — | — | — | — |
| Beverage emulsion type "Cola" | — | — | 0.05 | — | — | — | — |
| Phloretin | — | — | — | 0.0005 | — | 0.0005 | 0.01 |
| Hesperetin | 0.00075 | — | 0.00075 | 0.0012 | — | 0.00075 | 0.01 |
| Homoeriodictyol-Na | — | — | 0.005 | 0.005 | — | — | — |
| Water | | | | Ad 100 | | | |

The components were mixed in the indicated order and filled up with water to 100%. The mixtures were filled into glass bottles and carbonated.

Example 5

Hard candy (indications in % by weight)

| Ingredients | A | B | C | D |
|---|---|---|---|---|
| Sugar | 74.50 | — | — | — |
| Palatinit, Type M | — | 74.00 | 75.50 | 75.00 |
| Citric acid | 0.5 | 1.0 | 0.5 | — |
| Colour, yellow | — | 0.01 | — | — |
| Colour, red | — | — | 0.01 | — |
| Colour, blue | 0.01 | — | — | 0.01 |
| Peppermint aroma | 0.1 | — | — | 0.1 |
| Citrus aroma | — | 0.1 | — | — |
| Red berry aroma | — | — | 0.1 | — |
| Substance mixture C containing maltodextrins of example 1 | 0.01 | 0.012 | 0.015 | 0.008 |
| Balansin A | — | 0.005 | 0.010 | 0.005 |
| Hesperetin | — | 0.001 | 0.0005 | — |
| Phloretin | — | 0.002 | — | — |
| Wasser | ad 100 | ad 100 | ad 100 | ad 100 |

Steviol glycoside/Maltodextrin mixture (80:20) by the company Pure Circle

Example 6

| Yoghurt with a low fat content (indication in % by weight) | | | | |
|---|---|---|---|---|
| Ingredients | A | B | C | D |
| Sucrose | 10 | 8 | 6 | — |
| Sucralose | — | 0.02 | — | 0.2 |
| Rebaudioside A >95% | — | — | 0.025 | — |
| Saccharin | — | — | — | 0.3 |
| Substance mixture D containing maltodextrins of example 1 | 0.01 | 0.012 | 0.02 | 0.1 |
| Sour cherry extract according to example 1 | 0.2 | 0.1 | 0.2 | 0.2 |
| Hesperetin | | 0.001 | | 0.002 |
| Phloretin | — | — | 0.002 | |
| Homoeriodictyol sodium salt | — | — | — | 0.005 |
| Yoghurt, 0.1% fat | | Fill up to 100% | | |

Example 7

| Fruit gums (indications in % by weight) | | | |
|---|---|---|---|
| Ingredients | A | B | C |
| Saccharose | 34.50 | 8.20 | 34.50 |
| Glucose syrup, DE 40 | 31.89 | 30.09 | 31.89 |
| Substance mixture E containing maltodextrins of example 1 | 0.01 | 0.012 | 0.01 |
| iso Sirup C* Tru Sweet 01750 (Cerestar GmbH) | 1.50 | 2.10 | 1.50 |
| Gelatine 240 Bloom | 8.20 | 9.40 | 8.20 |
| Polydextrose (Litesse ® Ultra, Danisco Cultor GmbH) | — | 24.40 | — |
| Colour | 0.01 | 0.01 | 0.01 |
| Citrus aroma | 0.20 | — | 0.20 |
| Cherry aroma | — | 0.10 | — |
| Hesperetin | 0.0075 | — | |
| Water | ad 100 | ad 100 | ad 100 |

Example 8

| Sugar-free chewing gum (indications in % by weight) | |
|---|---|
| Ingredients | content |
| Gum base | 30.00 |
| Sorbitol powder | Ad 100 |
| Substance mixture F containing maltodextrins of example 1 | 0.1 |
| Palatinit | 9.50 |
| Xylitol | 2.00 |
| Mannitol | 3.00 |
| Aspartam | 0.10 |
| Acesulfam K | 0.10 |
| Emulgum/Emulsifier | 0.30 |
| Sorbitol 70% in water | 14.00 |
| Glycerol | 1.00 |
| Peppermint aroma | 1.50 |
| Hesperetin | 0.01 |

Example 9

| Custard (indications in g) | | | |
|---|---|---|---|
| Ingredients | A | B | C |
| Maize starch | 38 | 38 | 38 |
| Sugar | 38 | 30 | 22.8 |
| Substance mixture G containing maltodextrins of example 1 | — | 0.1 | 0.15 |
| Hesperetin | | | 0.03 |
| Vanilla aroma (Symrise) | 0.2 | 0.2 | 0.2 |
| Quinoline yellow | 0.02 | 0.02 | 0.02 |
| Milk | 500 | 500 | 500 |

The invention claimed is:

1. A substance mixture comprising compounds of general formula (I),

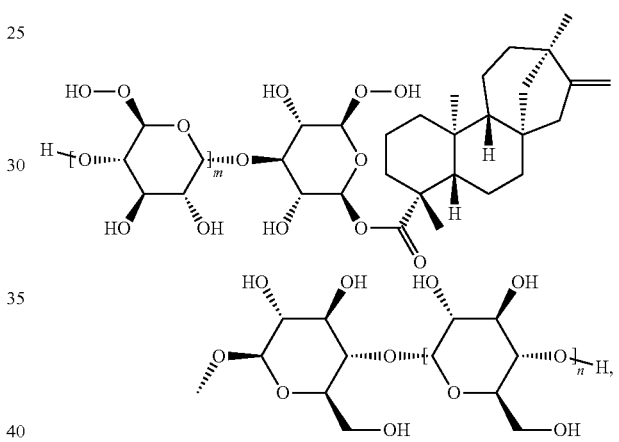

(I)

wherein m and n independently represent 0 to 50, the substance mixture comprising:
- (a1) less than 50% by weight rubusoside (m+n=0),
- (a2) more than 10% by weight alpha-glycosyl rubusosides with a total of 3 glucose units (m+n=1),
- (a3) more than 15% by weight alpha-glycosyl rubusosides with a total of 4 glucose units (m+n=2),
- (a4) more than 5% by weight alpha-glycosyl rubusosides with a total of 5 glucose units (m+n=3), and
- (a5) less than 6% by weight steviol monoside,
wherein the amount of all components (a1) to (a5) together adds up to at least 80% by weight and the remaining amount comprises water, glycerol, starch degradation products, proteins, fatty acids and/or fatty acid esters.

2. The mixture according to claim 1, wherein the starch degradation products comprise 3 to 100 alpha-1,4-linked D-glucopyranosyl groups.

3. The mixture according to claim 1, wherein the mixture additionally comprises one or more phenolic, naturally occurring sweet-enhancing aroma substances selected from the group consisting of hesperetin, phloretin, 1-(2,4-Dihydroxyphenyl)-3-(3-hydroxy-4-methoxyphenyl)-propan-1-one, 5-Hydroxy-4-(4-hydroxy-3-methoxyphenyl)-7-methoxy-2-chromanone, and mixtures thereof.

4. The mixture according to claim 1 comprising:
(a1) less than 30% by weight rubusoside (m+n=0),
(a2) more than 15% by weight alpha-glycosyl rubusosides with a total of 3 glucose units (m+n=1),
(a3) more than 18% by weight alpha-glycosyl rubusosides with a total of 4 glucose units (m+n=2),
(a4) more than 10% by weight alpha-glycosyl rubusosides with a total of 5 glucose units (m+n=3), and
(a5) less than 2.5% by weight steviol monoside,
wherein the amount of all components (a1) to (a5) together adds up to at least 80% by weight and the remaining amount comprises water, glycerol, starch degradation products, proteins, fatty acids and/or fatty acid esters.

5. A method for the production of aroma substances comprising incorporating a mixture according to claim 1 into an oral preparation.

6. A method for improving, enhancing or conveying the sweet taste and/or for masking an unpleasant taste impression of sweeteners comprising incorporating a mixture according to claim 1 into an oral preparation.

7. An aroma composition comprising a mixture according to claim 1.

8. An orally consumable preparation comprising a mixture according to claim 1.

9. A process for the production of a substance mixture according to claim 1, comprising combining alpha-cyclodextrin glucanotransferase in a transglucosylation reaction with a 1,4-glycosidic carbohydrate.

\* \* \* \* \*